(12) United States Patent
Garms et al.

(10) Patent No.: US 6,778,681 B2
(45) Date of Patent: Aug. 17, 2004

(54) ANALYSIS AND PRESENTATION OF INTERNAL FEATURES OF LOGS

(75) Inventors: Walter I. Garms, Palo Alto, CA (US); James M. Carver, San Martin, CA (US)

(73) Assignee: InVision Technologies, Inc., Newark, CA (US)

( * ) Notice: Subject to any disclaimer, the term of this patent is extended or adjusted under 35 U.S.C. 154(b) by 340 days.

(21) Appl. No.: 09/851,840

(22) Filed: May 9, 2001

(65) Prior Publication Data

US 2002/0168083 A1 Nov. 14, 2002

(51) Int. Cl.[7] .................................................. G06K 9/00
(52) U.S. Cl. ....................... 382/100; 382/131; 382/132; 382/141; 382/274; 382/169; 378/195; 198/460.1; 209/589
(58) Field of Search ................................ 382/100, 128, 382/131, 132, 141, 300; 378/199, 195, 57, 5; 198/460.1; 144/248.4; 209/589

(56) References Cited

U.S. PATENT DOCUMENTS

| | | | | |
|---|---|---|---|---|
| 3,815,738 A | * | 6/1974 | Sweet et al. ................ 209/518 |
| 4,135,247 A | | 1/1979 | Gordon et al. .............. 364/414 |
| 4,225,789 A | * | 9/1980 | Albrecht ........................ 378/5 |
| 4,283,629 A | | 8/1981 | Habermehl et al. ....... 250/455 T |
| 4,879,659 A | * | 11/1989 | Bowlin et al. .............. 700/167 |
| 4,879,752 A | | 11/1989 | Aune et al. ............. 382/455 T |
| 4,916,629 A | | 4/1990 | Bogue et al. |
| 5,023,805 A | | 6/1991 | Aune et al. ................. 364/507 |
| 5,135,037 A | * | 8/1992 | Wijesinghe ................. 144/357 |
| 5,182,764 A | * | 1/1993 | Peschmann et al. .......... 378/57 |
| 5,257,101 A | * | 10/1993 | Lee .............................. 348/95 |
| 5,262,946 A | * | 11/1993 | Heuscher .................... 378/15 |
| 5,262,956 A | | 11/1993 | DeLeeuw ............... 364/474.13 |
| 5,367,552 A | * | 11/1994 | Peschmann .................. 378/57 |
| 5,394,342 A | | 2/1995 | Poon .......................... 364/558 |
| 5,406,770 A | * | 4/1995 | Fikacek ......................... 53/54 |
| 5,412,220 A | | 5/1995 | Moore ......................... 250/563 |
| 5,433,150 A | * | 7/1995 | Long, Jr. et al. ......... 105/163.2 |
| 5,518,106 A | * | 5/1996 | Allard ....................... 198/459.5 |
| 5,544,558 A | * | 8/1996 | Hughes ..................... 83/75.5 |
| 5,765,617 A | | 6/1998 | Mierau et al. ............. 144/387 |
| 5,960,104 A | | 9/1999 | Conners et al. ............ 382/141 |
| 5,982,843 A | * | 11/1999 | Bailey et al. .................. 378/4 |

(List continued on next page.)

OTHER PUBLICATIONS

Daniel L. Schmoldt, "CT Imaging, Data Reduction, and Visualization of Hardwood Logs", *Hardwood Symposium Proceedings*, May 8–11, 1996, pp. 69–80.

Daniel L. Schmoldt, et al., "Nondestructive Evaluation of Hardwood Logs: CT Scanning, Machine Vision and Data Utilization", *Nondest. Test. Eval.*, vol. 15, pp. 279–309, 1999 Overseas Publishing Association N.V.

*Primary Examiner*—Timothy M. Johnson
*Assistant Examiner*—Barry Choobin
(74) *Attorney, Agent, or Firm*—Bever, Hoffman & Harms, LLP; James E. Parsons

(57) ABSTRACT

Systems and methods for non-intrusive analysis and display of internal features of wooden objects are provided. In embodiments of the system, a log is passed through a CT scanner in one continuous motion. One or more x-ray sources revolve around the log generating x-ray beams that traverse contiguous cross-sections of the log. An array of x-ray detectors detects x-rays that traverse the log for variations in the attenuation of rays. The detected attenuation is converted into spiral scan data that corresponds to projections in different contiguous cross-sections traversed by the x-rays. An image processor reconstructs spiral scan data into two dimensional cross-sectional images of the log by processing and formatting scan data using a planar reconstruction technique. The system renders three-dimensional views based on two-dimensional images.

56 Claims, 10 Drawing Sheets

U.S. PATENT DOCUMENTS

| | | | |
|---|---|---|---|
| 6,112,784 A * | 9/2000 | Lough ........................ | 144/195.1 |
| 6,151,379 A | 11/2000 | Kullenberg et al. ............ | 378/54 |
| 6,157,698 A | 12/2000 | Pietikainen et al. ........... | 378/58 |
| 6,176,283 B1 * | 1/2001 | Knerr ........................ | 144/248.4 |
| 6,217,214 B1 | 4/2001 | Cabral et al. ................ | 378/196 |
| 6,220,423 B1 * | 4/2001 | Gagnon et al. ............ | 198/460.1 |
| 6,229,872 B1 | 5/2001 | Amos | |
| 6,345,113 B1 * | 2/2002 | Crawford et al. ............ | 382/131 |
| 6,418,189 B1 * | 7/2002 | Schafer ........................ | 378/57 |
| 6,422,806 B1 * | 7/2002 | Jenkins et al. ............ | 414/795.2 |
| 6,430,255 B2 | 8/2002 | Fenkart et al. | |
| D474,706 S | 5/2003 | Kresse et al. | |
| 6,590,956 B2 | 7/2003 | Fenkart et al. | |
| 6,597,761 B1 | 7/2003 | Garms, III | |
| 6,647,091 B2 | 11/2003 | Fenkart et al. | |
| 6,690,766 B2 | 2/2004 | Kresse | |
| 2002/0071524 A1 * | 6/2002 | Renkart et al. ............... | 378/199 |

* cited by examiner

ANALYSIS AND PRESENTATION OF INTERNAL FEATURES OF LOGS

BACKGROUND

1. Field of Invention

The present invention is directed to non-intrusive analysis and visual display of internal features of logs and, in particular, to systems and methods for scanning, detecting, and displaying internal features of a log, using computerized tomography.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Related Art

The value of a board generally depends on the size of the board and number of defects in the board. Accordingly, sawmills, particularly when sawing valuable logs, attempt to maximize the yield of boards having large areas that are relatively free of defects. Naturally, a log with fewer defects provides better quality boards or lumber. Therefore, the commercial value of a log directly depends on the type and number of defects in the log.

Defects in a log commonly correspond to variations in a log's composition or density. Such variations often arise from the natural growth process of the tree and correspond to knots, voids, or decay in the body of the tree. Some defects such as cracks or decay on the exterior of a log are clearly visible, but many internal defects or the extent thereof (e.g., interior decay and internal knots) are not fully visible to the naked eye. A buyer, typically, evaluates a log by considering the log's shape, external indicators of internal defects, and knowledge of lumber grades. While experts such as log graders and sawyers are highly skilled in the evaluation of logs, they cannot possibly detect all internal defects of a log. Therefore, it is difficult to accurately distinguish a high quality log over a lower quality log that has a similar external appearance.

A person could more accurately estimate the value of a log if he could view and inspect the internal defects and undesirable features of the log. Accordingly, methods and systems that can efficiently detect and reveal the defects in the interior composition of a log with reasonable accuracy would be very helpful in evaluating a log's worth.

SUMMARY

One or more embodiments of the invention are directed to a system and method for non-intrusive analysis and visual display of the internal features of logs, using CT scanning technology. The system and method described herein may be also applicable to scanning objects other than a log. In one embodiment of the system, a log passes through a CT scanner in one continuous motion. The scanner includes an aperture to receive the log and one or more x-ray sources that revolve around the log, as it passes through the system, generating x-ray beams that traverse multiple cross-sections of the log.

An array of x-ray detectors detects attenuation of the x-ray beams that traverse the log. The attenuation of the x-ray beams is measured based on changes in the intensity of the x-ray beams as they pass through the log. These measurements are converted into scan data. The scan data contains information about multiple cross-sections of the log. A computer system reconstructs the scan data into two-dimensional or cross-sectional images of the log, by using a standard planar CT reconstruction technique.

The computer system also uses the scan data collected from multiple cross sections to construct three-dimensional images of the log. A three-dimensional image data set, in accordance with one aspect of the system, can thus be produced from data from two-dimensional images. In certain embodiments, interpolation, surface rendering, and ray tracing techniques may be used to produce three-dimensional image data sets, as well. In certain embodiments of the invention, three-dimensional image data sets are used to produce two-dimensional images with three-dimensional features using perspective and shading techniques.

According to one or more aspects of the invention, the system includes a retractable log driver (Push Dog) that drives the log on a transport bed through the scanner. In certain embodiments, the transport bed is preferably constructed of at least two parallel metal rails. The rails have a gap in the area where the x-rays pass through to avoid image distortion and interference with the scanning process. A loader or loading arm coupled to a mechanical actuator loads a log from a staying mechanism onto the transport bed. The loading arm, in a certain embodiment, includes one or more rails that form a portion of the transport bed when the loading arm is engaged in a loaded position. The loading arm can be activated in multiple positions to receive, load, or eject a log.

Embodiments of the system include an unloading arm for unloading logs from the transport bed onto a receiving mechanism. The receiving mechanism transitions the logs to a storage area, for example. The staying and receiving mechanisms can be represented by a variety of devices (e.g., "transport", "log haul", "hourglass rollers", "log kicker, etc.). The unloading arm may also include one or more rails that form a portion of the transport bed.

Before the log driver engages the log, a sensor mechanism determines whether a log loaded on the system can go through the aperture of the CT scanner. If the sensor detects an oversized log, the log is ejected from the transport bed. In certain embodiments, the log is ejected when the loading arm moves to an eject position. If the sensor determines that the log can safely clear the aperture of the scanner, then the log driver engages at least one end of the log and drives the log through the scanner. The driver is configured to displace the log at a speed that allows the scanning system to capture sufficient data from multiple cross-sections of the log for display and analysis purposes.

A processing system converts captured data, also referred to as scan data, into two or three-dimensional density distribution images that display the defects within the body of the log so that the defects are recognizable by a human operator or a computing system. In one or more embodiments, an end unit (e.g., hold back dog) engages the log at the end opposite to the point of engagement of the log driver to add stability to the positioning and movement of the log on the transport bed. Once the complete length of the log has been driven through the scanner, the log driver is retracted to its original position so that another log can be loaded. The end unit can further include marking systems that mark the log for sawing or identification.

Other embodiments of the invention may include a revolving belt mechanism with multiple log drivers installed at successive intervals around the belt so that a second log driver is in position to engage a second log when the scanning process for the first log is complete. This avoids the requirement for having a retracting mechanism. In either implementation, the loading arm is configured in such a way to allow for loading a second log immediately after the first log has gone through the scanning process.

The scan data and the images produced as the result of CT scanning and reconstruction are useful to a log purchaser or sawyer to evaluate the worth and usefulness of the log for producing certain quality boards. For example, the system can reconstruct scan data to simulate a longitudinal cut through the log producing the image of a virtual board. The system can also reconstruct other images such as three-dimensional views of the log that display the interior defective regions of the log, the type of defect (e.g., decay, cracks, knots, etc.), and the exact location of each undesirable feature.

Certain images, according to an embodiment of the invention, are produced so that the exterior surface of the log appears transparent and defects appear opaque and/or color-coded so that the defects are easily identified. In accordance with one aspect of the invention, the system may determine an optimal cutting solution for the log based on information provided about the log's intended use, the type of each defect, and respective distance between the defects. Other embodiments may provide a purchaser with a log's grade, estimated value, or most suitable or profitable cutting solution.

In accordance with another aspect of the invention, a log is marked with a reference mark that indicates the orientation of the log during the scanning process. This information can be used during sawing or image processing to accurately identify the location of the defective or undesirable regions in the log. Using a reference mark, a sawyer or a computerized sawing machine can appropriately position the log's orientation for a specific cut. The reference mark can be simple stripes or markings painted on one or both ends of the log. The markings can include more sophisticated coding such as bar codes or magnetic strips that contain additional information about the log (e.g., grade, sample cross-sectional views, sawing solutions, etc.). The reference marks can be placed on the logs by a marking mechanism. In one embodiment of the system, the marking mechanism is integrated into the log driver, end unit, or both.

DETAILED DESCRIPTION

The invention relates to a system and method for scanning, detecting, and displaying internal features in a log by using computerized tomography (CT) techniques. One skilled in the art will appreciate that the teachings of the present invention can be equally applied to the detection and display of inner features of any object using any scanning technology. In the following description, numerous specific details are set forth to provide a more thorough description of embodiments of the invention. The invention, however, may be practiced without some or all of these specific details. In some instances, certain well-known features have not been described in detail so as not to obscure the more relevant aspects of the invention.

System Architecture Overview

Figure 1:
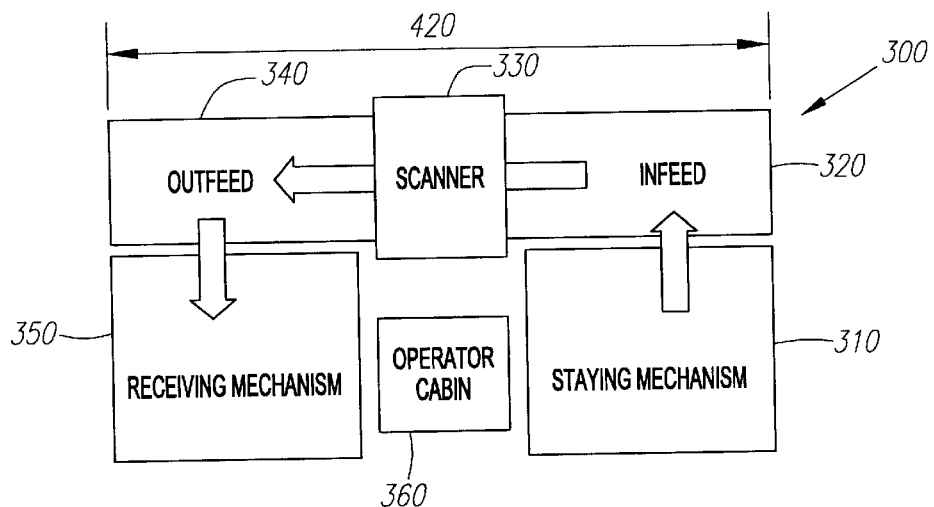
FIG. 1 is a block diagram illustrating components of a log scanning system in accordance with an embodiment of the invention.

In accordance with one or more aspects of the system, a CT scanner in combination with a computing system and other corresponding equipment is used to scan and graphically display the interior defects in a log in a manner that is recognizable by a human operator. FIG. 1 is a block diagram illustrating the primary components of the system. As shown, system 300 generally includes a first staying mechanism 310, an infeed structure 320, a CT scanner 330, an outfeed structure 340, and a receiving mechanism 350. An operator cabin 360 may be also included in embodiments of the system between transport mechanisms 310 and 350, for example, to house the computing system and control mechanisms that operate the above components of the system.

Figure 2:
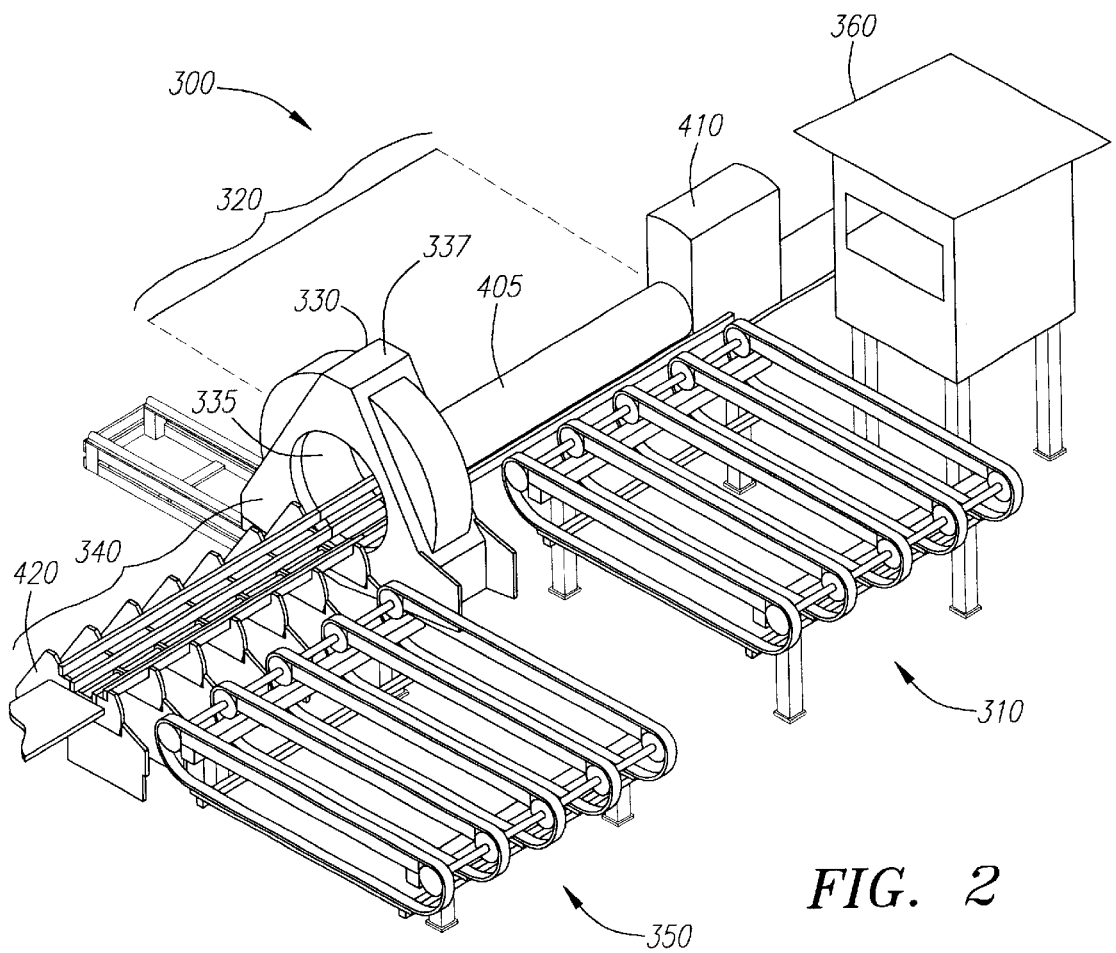
FIG. 2 is a perspective view of the system of FIG. 1, in accordance with one or more embodiments.

Infeed structure 320, scanner 330, and outfeed structure 340 include rails, in certain embodiments of the system, that are longitudinally aligned on a substantially horizontal plane to collectively compose a transport bed 420 (FIG. 2). The rails, in certain embodiments, are straight and parallel but aligned along a curved surface to form transport bed 420 such that the rails can support and cradle the outer surface of a log. Transport bed 420 in certain embodiments is a continuous medium that supports and guides a log through scanner 330.

Staying mechanism 310 is utilized to transport one or more logs from a storage area to infeed structure 320. The logs, before being placed on staying mechanism 310, can be debarked and readied for scanning. Infeed structure 320, as described in further detail below, includes mechanical components for receiving a log from staying mechanism 310 and driving the log through scanner 330. Scanner 330 is an electromagnetic or x-ray scanner capable of scanning a log to detect defects. Outfeed structure 340 unloads logs from system 300 onto receiving mechanism 350. Receiving mechanism 350 is a transport mechanism, similar in structure to staying mechanism 310. Receiving mechanism 350, however, operates in a reverse direction to transfer a log back to the storage area, for example.

FIG. 2 is a perspective view of an embodiment of system 300 with operator cabin 360 located at a closer proximity to infeed structure 320 and further away from outfeed structure 340. As shown, in accordance with one or more aspects of the invention, transport mechanisms 310 and 350 include conveyor or chain driven mechanisms for transporting multiple logs to and from the scanning area. Infeed structure 320 and outfeed structure 340 include rails that extend through scanner 330 to form transport bed 420. Transport bed 420 is preferably constructed out of a plurality (e.g., four) of parallel steel rails that extend along the log's path through scanner 330 to support and guide the log's movement. The rails may be made of any suitable material (e.g., steel) that can smoothly support movement of the log on transport bed 420. In accordance with one aspect of the invention, system 300 includes a tunnel structure for shielding a human operator from harmful radiation generated by scanner 330.

Scanning System and Method

Figure 3:
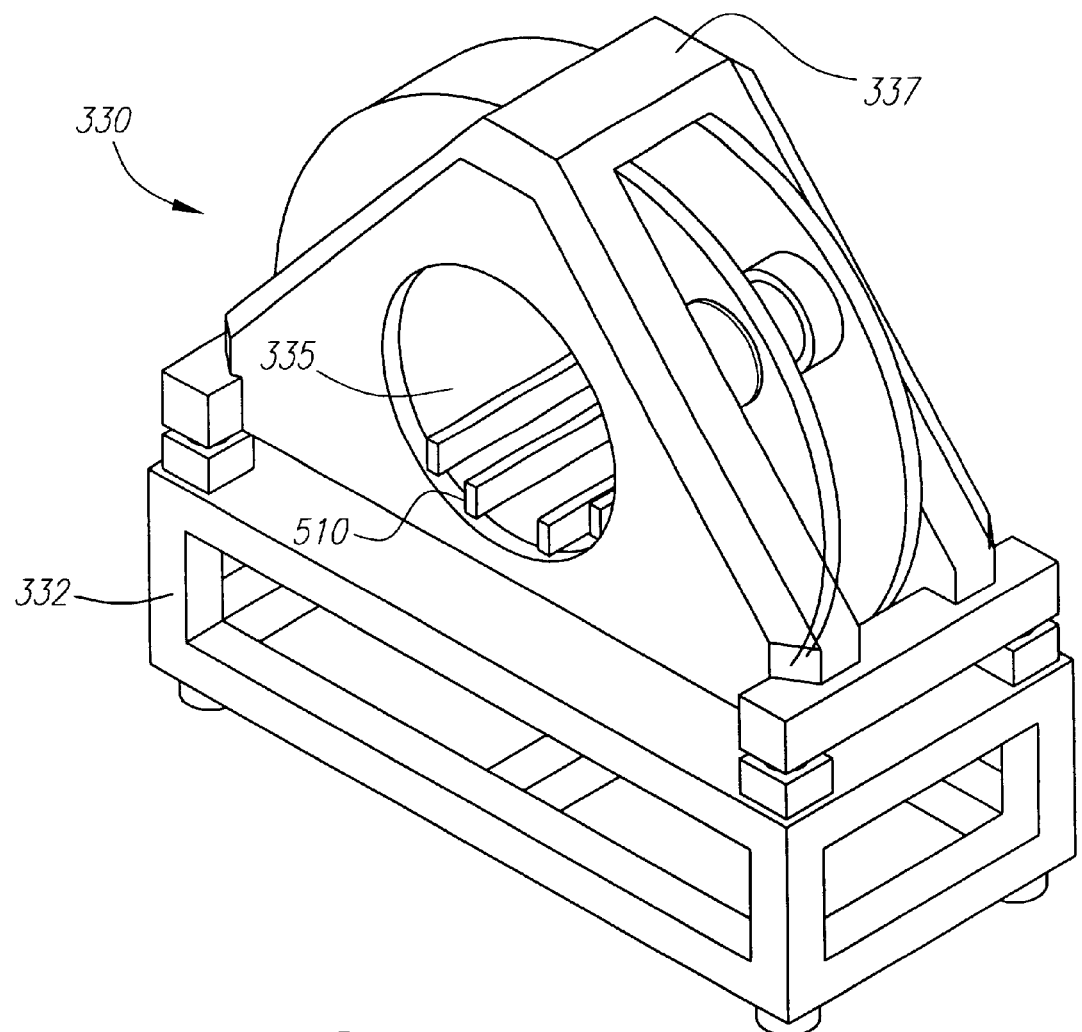
FIG. 3 illustrates a perspective view of a log CT scanner, according to an embodiment of the invention.

Scanner 330, illustrated in further detail in FIG. 3, is a CT scanner (e.g., CTX-5000, CTX 9000, CTX 9300 scanning unit manufactured by Invision Technologies, Newark, Calif.). Other scanning mechanisms that utilize electromagnetic radiation to calculate density distribution within selected cross-sections or regions of an object may also be utilized. Scanner 330 is between infeed 320 and outfeed 340. Scanner 330 includes a gantry 337 with an opening in form of aperture 335 to receive a log 405. As shown in FIG. 3, scanner 330 can have a stand-alone structure that can be functionally integrated with infeed and outfeed structures 320 and 340 to provide a continuous transport bed 420 for a log to travel on. In embodiments of the invention, scanner 330 includes base frame 332 for mounting gantry 337 at a height suitable for receiving a log 405 from infeed 320.

Aperture 335 is preferably circular in shape and preferably has a diameter of 85 to 110 centimeters to receive logs of approximately 25 to 100 centimeters in diameter, for example. As described in further detail below, log driver 410 (FIG. 2) is a driving mechanism utilized for driving log 405 through aperture 335. Log driver 410 engages and pushes log 405 so that log 405 moves in a controlled continuous manner along transfer bed 420 in an axial direction. In embodiments of the invention, oversized logs that cannot fit through aperture 335 are detected and unloaded before log driver 410 engages the oversized log.

Figure 4A:
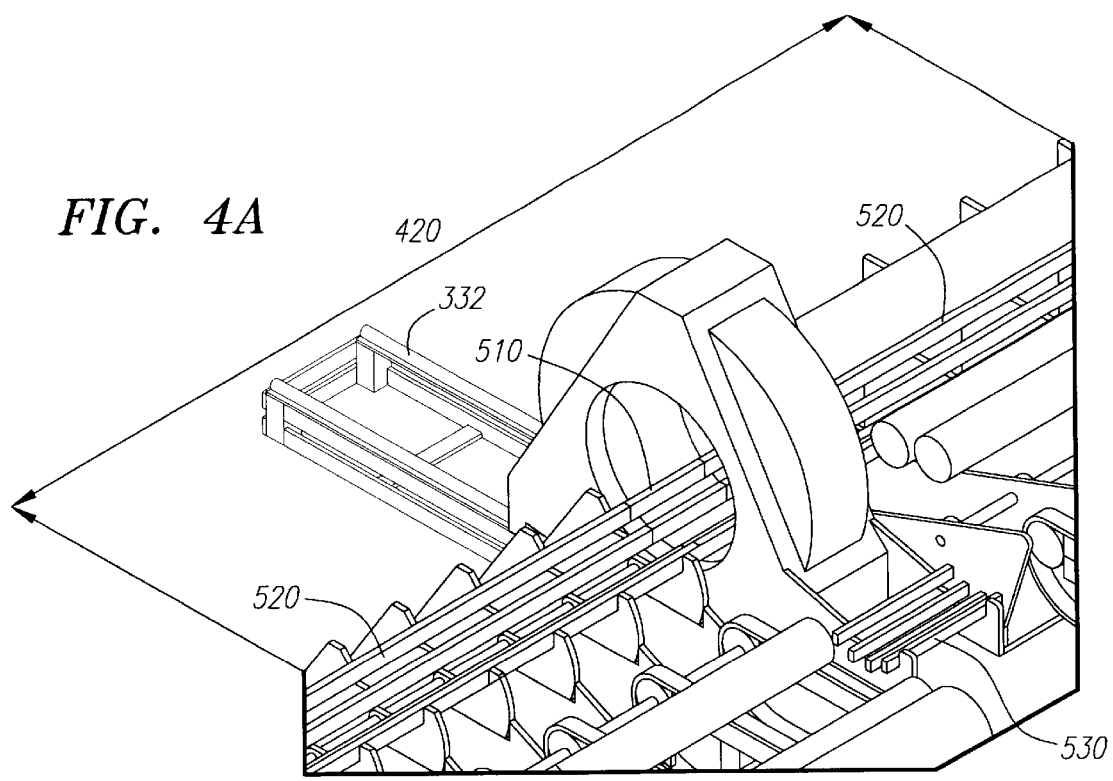
FIGS. 4A and 4B illustrate the log CT scanner of FIG. 3, according to an embodiment of the invention, in mount and dismount positions.
Figure 4B:
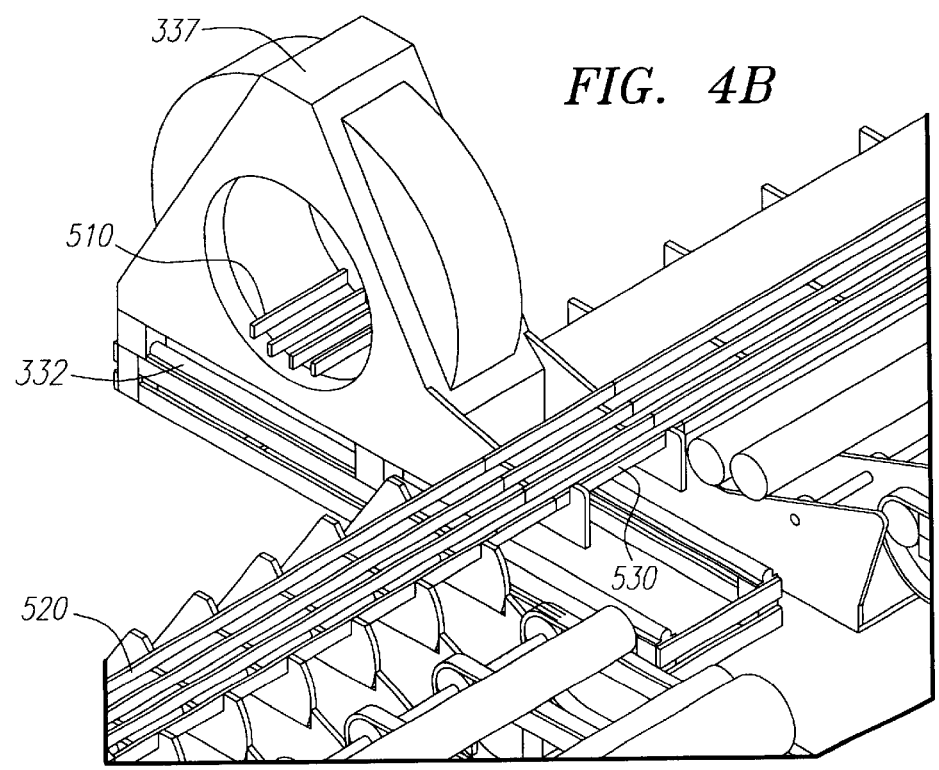

FIGS. 4A and 4B illustrate a system according to an embodiment of the invention in which a scanner 330 can move between a mounted position and a dismounted position. This movable scanner allows the transport of oversized logs from infeed 320 to outfeed 340 without having to drive the log through scanner 330.

FIG. 4A illustrates scanner 330 in the mounted position. In certain embodiments, scanner 330 includes guide rails 510 that extend in a substantially horizontal plane through scanner 330. Guide rails 510 optionally include a gap to prevent guide rails 510 from interfering with X-rays projected through the log during scanning. As shown, infeed 320 and outfeed 340 include matching horizontal rails 520. In this embodiment, each of guard rails 510 lines up with a matching one of rails 520 when scanner 330 is in the mounted position. Rails 510 and 520 are positioned along a curved surface to cradle the log and resist movement of the log perpendicular to the lengths of the rails. In the mounted position, guide rails 510 engage rails 520 forming one continuous transport bed 420 (possibly including a small gap in a scanning region inside scanner 330). Guide rails 510 help to guide and support the controlled movement of log 405 in an axial direction from infeed 320 through scanner 330 and over to outfeed 340.

In certain embodiments, to maximize the signal to noise ratio of the scan data and avoid any gap in transport bed 420, all or a portion of guide rails 510 and/or rails 520 are made of low attenuation material (e.g., plastic) that is not highly detectable by scanner 330. Alternatively, some embodiments of the system have a gap in guide rails 510 inside scanner 330. The gap is sufficiently wide (e.g., about 1 cm) to allow an unobstructed scanning region within scanner 330 such that an x-rays generated by the scanner 330 do not traverse guide rails 510 during the scanning process.

FIG. 4B illustrates the system when scanner 330 is in the dismounted position. In accordance with one or more aspects of the invention, a base frame 332 extends out in a direction substantially perpendicular to the direction of movement of log 405. Scanner 330 can move across the extension to clear transport bed 420. Certain embodiments of the invention include an external set of guide rails 530. In the dismounted position, guide rails 530 engage rails 520 forming one continuous transport bed 420. As such, an oversized log can be transported from infeed 320 to outfeed 340 without going through aperture 335.

This aspect of the invention is useful, for example, when a log loaded onto infeed 320 is too large to pass through aperture 335. Other embodiments that allow the removal of scanner 330 from path of travel of log 405 on transport bed 420 are possible. For example, an embodiment may include a lifting mechanism to lift scanner 330 above transport bed 420 at a height that would clear the log. Certain embodiments may include wheels under scanner 330 to allow removal of scanner 330 from in between infeed 320 and outfeed 340, respectively, so that an oversized log can be transported from one side to the other.

Figure 5:
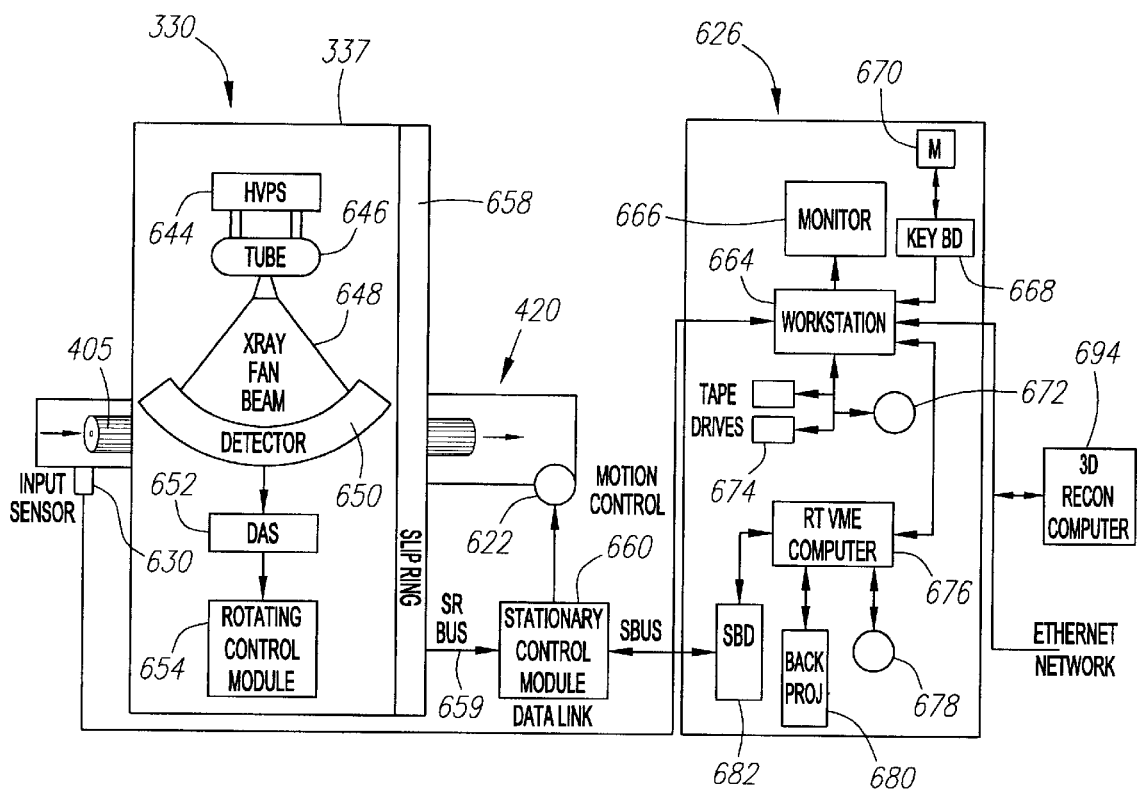
FIG. 5 is a block diagram illustrating the components of the scanner in conjunction with a corresponding computing system that processes the data produced by the scanner, in accordance with an embodiment of the invention.

FIG. 5 illustrates a block diagram of the various physical components of scanner 330 and a corresponding computing system 626. Scanner 330 scans logs for defects and produces scan data. Computing system 626 processes the scan data e.g., converts scan data to image data. Scanner 330 includes gantry 337, an x-ray source 646, a detector array 650, and a data acquisition system (DAS) 652. Gantry 337 houses a high voltage power supply (HVPS) 644 coupled to x-ray source 646. X-ray source 646 creates an x-ray fan beam 648 that traverses log 405 during scanning. Detector array 650 is opposite to x-ray source 646. Detector array 650 measures the intensity of x-rays that passed through log 405. Detector array 650 can include multiple detector elements, multiple segmented detector elements, an array of single detectors, or continuous media responsive to x-rays.

Detector array 650 intercepts x-rays attenuated by log 405 as the log passes through x-ray fan beam 648. The x-ray detectors in the detector array convert x-ray intensities into electrical signals. These electrical signals are digitized by the data acquisition system 652 to form scan data. Software in workstation 664 or back projector 680 manipulating the corresponding scan data produces cross-sectional images of the log which show the log's internal features. In certain embodiments of the invention, x-ray source 646 and detector array 650 revolve around log 405 during the scanning process.

Alternatively, x-ray source 646 and detector array 650 may remain stationary while log 405 axially rotates in the field of scan. In either implementation, log 405 moves at a constant linear speed relative to scanner 330 during the scanning process. In some embodiments, log 405 moves as described across a transport medium through scanner 330. In other embodiments, log 405 remains stationary and scanner 330 moves along the length of log 405 during the scanning process.

In the exemplary embodiments of the invention, log 405 continuously travels through fan beam 648, while x-ray source 646 revolves around log 405. As the result of the continuous movement of log 405 during the scanning process, a volume of attenuation measurements is taken that includes information about the cross-sections of log 405. In particular, scanning log 405 produces scan data that corresponds to a spiral slicing of log 405.

A portion of the spiral corresponding to all or part of one or more rotation around log 405 provides raw scan data for CT processing that determines a density distribution for a cross-section of log 405. The raw scan data produced, as the result of this continuous scanning, is sometimes referred to herein as spiral scan data. This is in contrast to conventional scanning methods that produce scan data that includes information about multiple distinct cross-sections in multiple parallel planes through the log.

Detector array 650 determines the spiral scan data by measuring the intensity of x-rays after the rays pass through the log, and computing system 626 converts the spiral scan data into the density distributions for cross-sections of the log. Because knots, bark, decay, sapwood, heartwood, voids, and other log features usually have different densities, these features can be distinguished based on detected variations in density. For example, a knot in the body of a log may have a higher density in comparison to a void or a crack. In one or more embodiments, the collection of the density distributions for evaluated set of cross-sections of the log forms a three-dimensional data structure sometimes referred to herein as the image data for the log. Images representing the inner features of the scanned log can be rendered from the image data.

In accordance with an aspect of the system, the spiral scan data is communicated to data acquisition system 652 and computing system 626. Computing system 626 processes the spiral scan data to generate the density distributions and images that identify and display the internal features of the log. The relationship between attenuation and density is linear in woody materials. Thus, higher density for a certain region may indicate a knot, for example, while lower density may indicate a crack in log's body. Detector array 650 is connected to data acquisition system 652. Data acquisition system 652 converts all detector measurements into spiral scan data in a digital format, for example. In embodiments of the system, data acquisition system 652 exchanges control signals with a rotating control module 654 that provides the means for x-ray source 646 to rotate about the scan object (e.g., log 405).

In embodiments of the invention, gantry 337 includes rotating control module 654 that controls the communication and transfer of data and power between the rotating and non-rotating portions of scanner 330. Rotating control module 654 is electrically coupled to the non-rotating portion of scanner 330 (e.g., stationary control module 660) via a slip ring 658 having multiple contacts. Through slip ring 658, electrical input power is transferred from HVPS 644 to other electrical component within gantry 337. Digital data signals and control signals are also transferred to and from gantry 337 through slip ring 658. In one or more embodiments of the invention, a wireless transmitting and receiving system (e.g., an RF Ring) transmits data and control signals between the rotating and non-rotating portions of the scanner and slip ring 658. By using slip ring 658, gantry 337 rotates continuously without the need to use winding/unwinding mechanisms to connect rotating components of the system to the stationary ones, via cables, for example. Slip ring 658 is coupled through a slip ring bus 659 to stationary control module 660. Stationary control module 660 provides control signals to scanner 330 and motion controller 622.

Image Reconstruction System and Method

In one or more embodiments of the invention, spiral scan data acquired by scanner 330 is transmitted to computing system 626 via stationary control module 660 for reconstruction into two or three-dimensional images or data structures. Images reconstructed from the spiral scan data correspond to cross-sections of the scanned portions of log 405. This cross-sectional data is analyzed by components of computing system 626, illustrated in FIG. 5, and is converted to image data. Computing system 626 includes a workstation 664. Workstation 664 is coupled to a monitor 666 for controlling the operation of various components of the system. A system operator interacts with the workstation 664 via a keyboard 668, a mouse 670, and/or other user interface devices. Memory device 672 and tape drives 674 are also provided, in accordance with one or more embodiments of the invention, for data storage.

In certain embodiments, a CT image reconstruction system processes the spiral scan data using a standard planar CT image reconstruction technique and ignore the longitudinal motion occurring during one rotation around log 405. Alternatively, special spiral scan reconstruction techniques can produce an accurate detailed image of a particular cross-section of an object. However, certain embodiments of the invention do not utilize a spiral reconstruction technique to determine density distributions because the overhead associated with using such reconstruction techniques is relatively high and not cost effective. As such, certain embodiments use standard planar CT reconstruction techniques to construct cross-sectional images of log 405. These well known techniques include Direct Fourier Reconstruction and Filtered Back Projection.

Generally, using a standard planar CT reconstruction technique to determine scan data from spiral scanning of an object can result in a distorted image that does not clearly or accurately distinguish between the internal features of the object. However, in accordance with one aspect of the invention, scanner 330 rotates around a log at about 60 rpm, while the movement of the log during a single rotation is about 5 cm. Other rotation and movement rates may be used as desired. Because wood composition is relatively consistent within successive cross-sections in a longitudinal direction, the movement during a scanning revolution does not greatly change the raw data. Additionally, features smaller than one cm are often of little interest.

Accordingly, a standard planar reconstruction method can produce images and density distributions that are sufficiently accurate for determining certain defects in the log. A planar reconstruction method, in contrast to more sophisticated and resource intensive methods, allows the system to operate with maximum throughput and efficiency while slightly compromising image quality. One embodiment of the invention uses a Direct Fourier Reconstruction method to reconstruct data obtained from preferably about 250° of rotation of x-ray source 646 around the log. This is equal to about 180° plus the x-ray fan angle. During the 250° rotation, the log moves approximately 3.5 cm.

In accordance with certain aspects of the system, the image of a cross-section of log 405 is constructed from the data acquired during 250° of rotation. Since the log is moving during data acquisition, half of the data is collected during the first 125° of rotation on either side of the selected cross section, so the image produced contains contributions from features on either side of the cross section. However, the reconstruction technique emphasizes the contributions of features scanned during the central 110° of rotation (i.e., 180°–fan angle). Although a single acquisition needs 250° of rotation, images can be reconstructed using overlapping data. For example, an image can be produced from scan data centered at about 90°, 180°, 270°, and 360° (plus the initial 70° corresponding to the fan angle) to produce 4 images per rotation.

Log 405 moves approximately 6 centimeters, for example, for every rotation of the x-ray source 646 to reconstruct images of cross-sections spaced 1.5 centimeters apart. Preferably, the cross-section determined using the above reconstruction method consists of an array of 512× 512 density values. Images of other cross-sections of the log are generated by linear interpolation of the density values for the points in between the reconstructed points. The above-referenced angles and distances are approximations and are provided by way of example. Of course, other rotation angles and distances may be used within the course and scope of this disclosure.

In certain embodiments, workstation 664 is preferably coupled to a real time VME computer 676 that provides additional mathematical computing power. The VME computer 676 preferably includes memory device 678. A back projector 680 is provided in conjunction with VME computer 676. Back projector 680 processes the spiral scan data to generate planar image data, in accordance with one aspect of the system. The image data may be displayed on monitor 666. As described above as an alternative to CT reconstruction using back projector hardware 680, the Direct Fourier Reconstruction method may be used. As is known in the art, such a method does not require a back projector 680, instead, standard computers or array processors are used, in one or more embodiments.

In accordance with one aspect of the invention, based on the density of certain defects, computing system 626 can be programmed to detect and display specific defects so that different defects can be easily distinguished from one another. For example, the system can be programmed to construct an image of the log where undesirable features of the log such as voids or decay are highlighted. Embodiments of the system are configured to display the heartwood or other desirable wood as translucent or transparent, for example. The internal undesirable features may be presented instead in various colors or opaque shades to indicate different types of defects. For example, voids and decay can be displayed as white, while knots can be displayed as black. Additionally, the physical appearance of the grain at certain longitudinal cross-sections can be simulated by generating a longitudinal cut through CT cross-sectional images in shades of brown, for example.

Exemplary Mechanical Embodiment of the System

Figure 6:
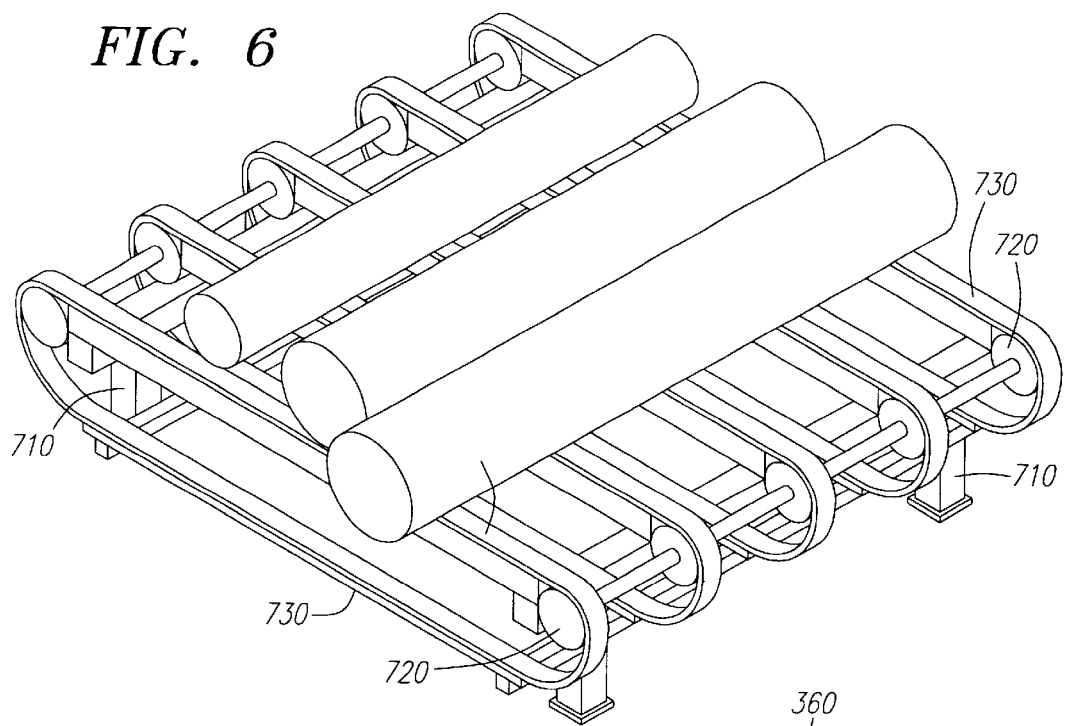
FIG. 6 illustrates a staying or receiving mechanism for transporting logs to and from a scanning system.

Aside from the novel aspects of the system directed to scanning and imaging, one or more aspects of the system are directed to a system and method for handling logs before, during, and after the scanning process. FIG. 6 illustrates a transport mechanism for transporting logs to and from transport bed 420, according to one or more embodiments of the system. Transport mechanisms 310 and 350, mentioned earlier, include a frame 710, a motor drive 720, and one or more conveying belts 730. Motor drive 720 is installed on frame 710 and includes an engine rotatably engaged to one or more rollers for rotating the rollers in a clockwise or counterclockwise direction. The rollers are preferably tapered inwardly (e.g., in the shape of an hourglass) to snugly receive belts 730. Belts 730 are tightly fit around the rollers to provide a conveying bed for carrying logs to and from system 300. In embodiments of the invention, other driving or power transferring mechanisms may be used to provide a non-binding conveying bed. For example, belts 730 maybe replaced by chains or other equivalents engaged to sprockets instead of rollers.

Figure 7:
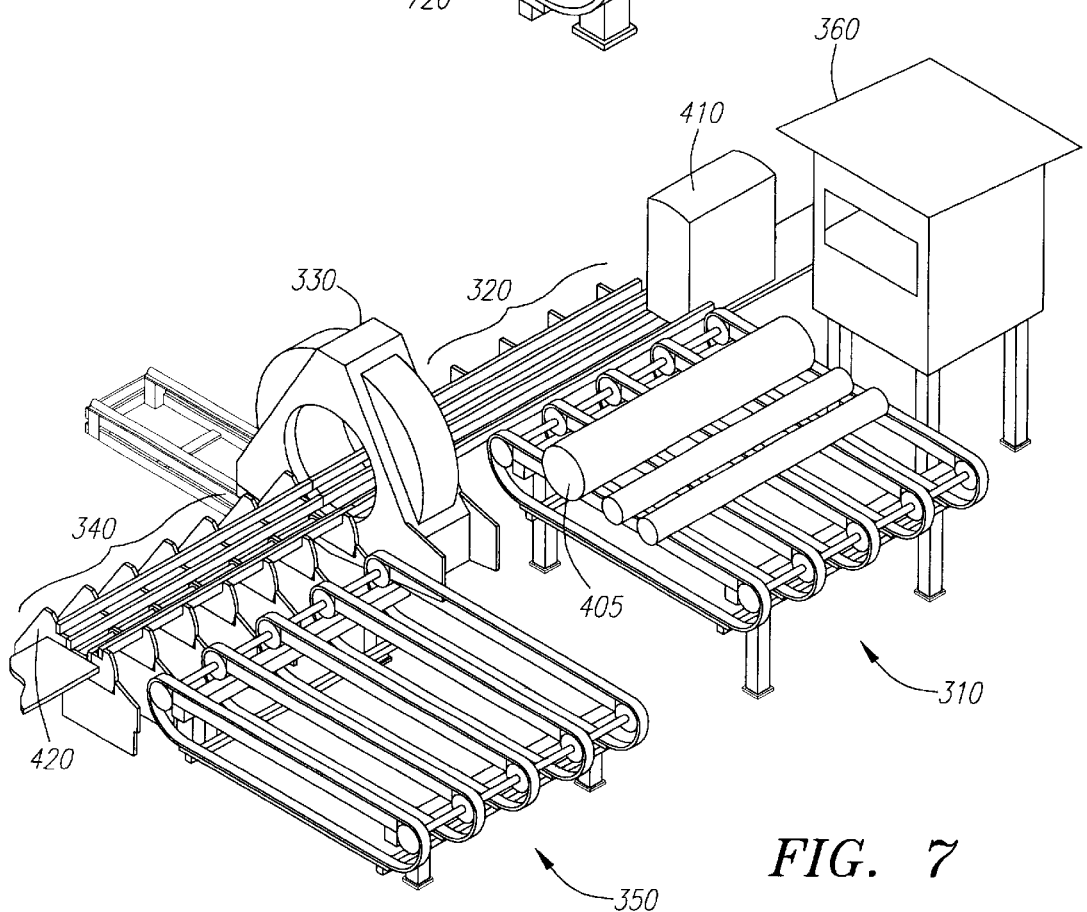
FIG. 7 is a perspective view of the system of FIG. 1 illustrating the loading arm in a receiving position, in accordance with an embodiment of the invention.

FIG. 7 illustrates transport mechanisms 310 and 350 in operational relationship with other system components, according to one or more embodiments. Staying mechanism 310 delivers logs to transport bed 420 for scanning. Receiving mechanism 350 receives scanned logs from transport bed 420 and moves the scanned logs away from transport bed 420. In certain embodiments of the invention, transport mechanisms 310 and 350 have the same construction but operate to move logs in different directions. Once staying mechanism 310 delivers log 405 system 300, system 300 performs a series of operations to load log 405 on transport bed 420. FIG. 7 illustrates the relative positions of components 310, 330, 350, and 420 of system 300 with respect to one another before log 405 is loaded onto transport bed 420. As shown, log driver 410 is in a retracted position ready to engage log 405 after log 405 is loaded.

Figure 8:
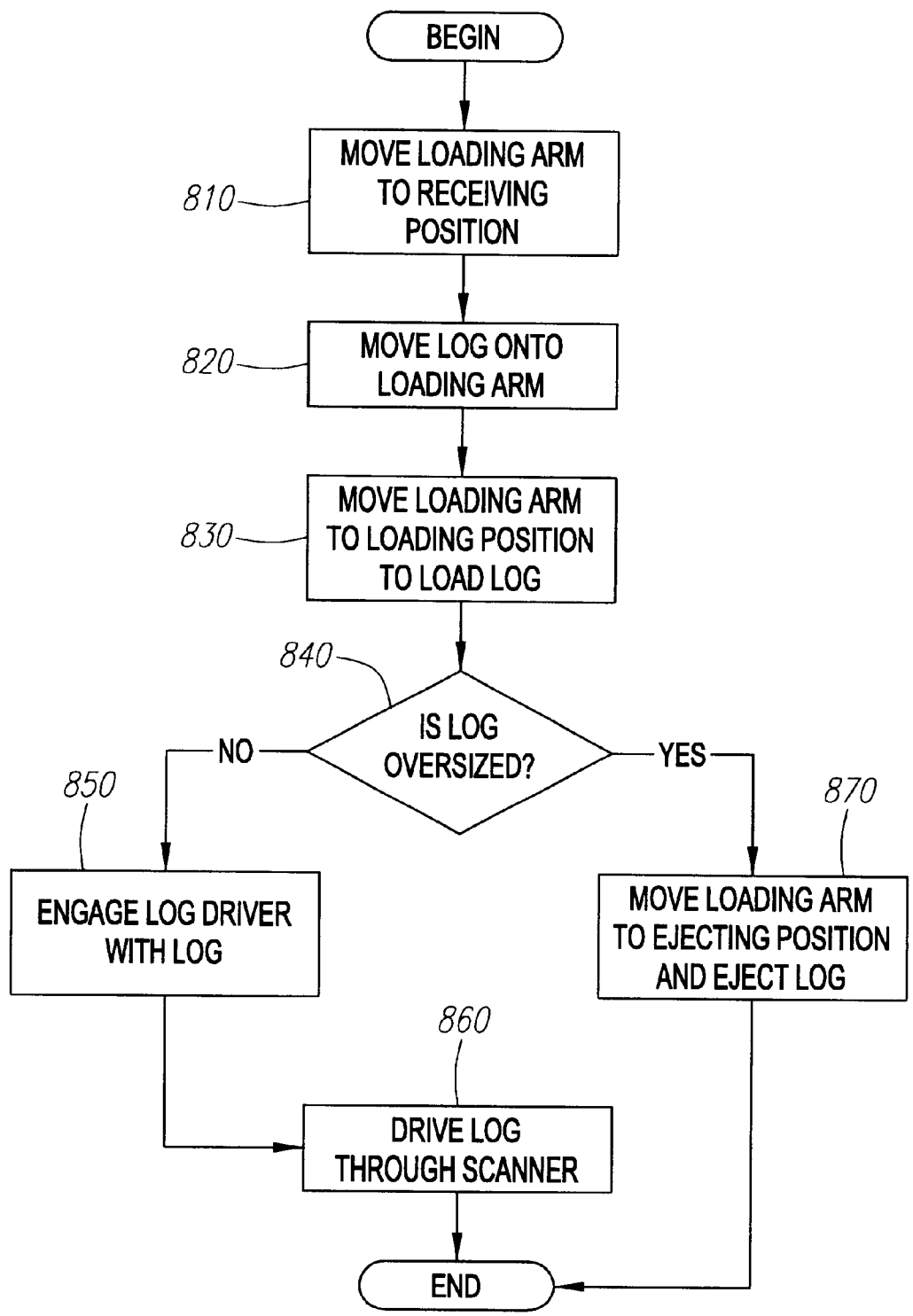
FIG. 8 is a flow diagram illustrating a method of processing logs for scanning by the system, according to an embodiment of the invention.
Figure 9A:
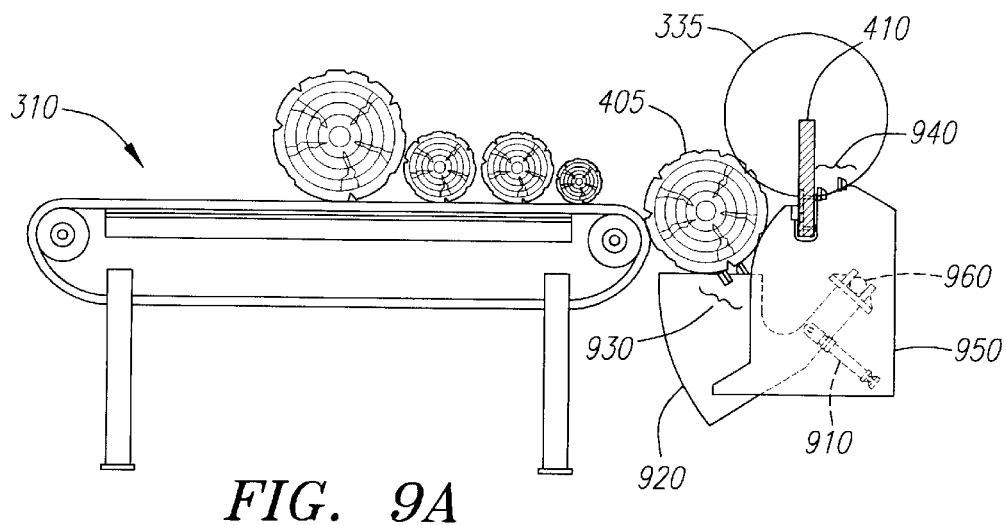
FIG. 9A is a cross-sectional view illustrating the loading arm in a receiving position in accordance with an embodiment of the invention.
Figure 9B:
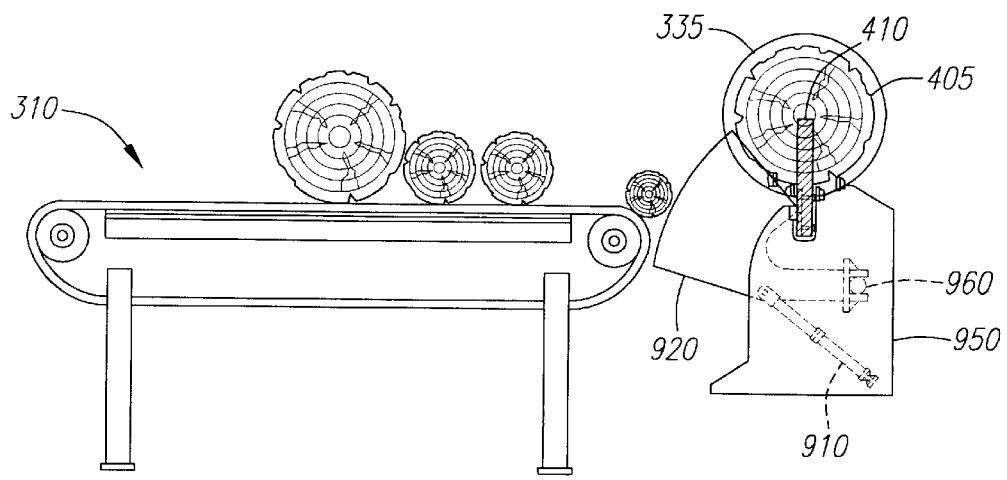
FIG. 9B is a cross-sectional view of the system illustrating the loading arm in a loading position.
Figure 9C:
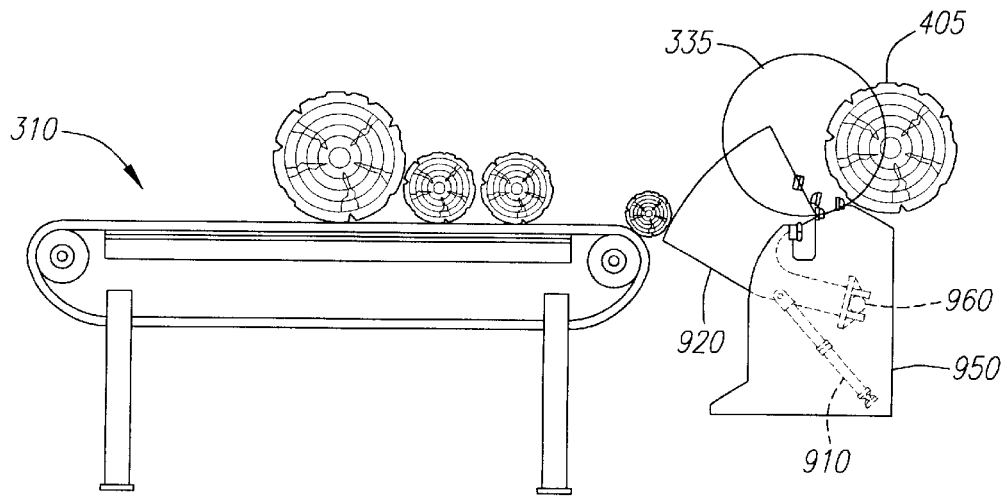
FIG. 9C is a cross-sectional view of the system illustrating the loading arm in an ejecting position.

FIG. 8 is a flow diagram illustrating a method of loading and unloading log 405 on transport bed 420, in accordance with one or more aspects of the invention. Transport bed 420, as described earlier, includes infeed and outfeed structures 320 and 340, with scanner 330 mounted there between. In certain embodiments, each of infeed 320 and outfeed 340 includes movable and non-movable parts. As shown in FIG. 9C, the movable part of infeed 320 includes a loading arm 920 that includes one or more rails 930. The non-movable part includes one or more rails 940 supported by a frame 950. FIGS. 9A through 9C include cross-sectional views of system 300 with loading arm 920 in three different positions. FIGS. 9A, 9B, and 9C illustrate loading arm 920 in a receiving position, a loading position, and in an ejecting position, in accordance with one or more aspects of the invention.

To load the logs transported from staying mechanism 310 onto transport bed 420, loading arm 920 is moved to a receiving position at step 810. Loading arm 920 is rotationally attached to an axle 960 supported by frame 950. Loading arm 920 and axle 960 are coaxial, sharing a common pivot point. By the virtue of this relationship, loading arm 920 rotates about axle 960, for example, through 180° by means of an actuator 910, such that loading arm 920 can be lowered into a receiving position to receive log 405 from staying mechanism 310. With loading arm 920 lowered, at step 820, log 405 moves or rolls onto loading arm 920 from staying mechanism 310, as the result of log 405 reaching the terminal end of the conveying belt of staying mechanism 310 and loading arm 920 being lower than the terminal end of staying mechanism 310.

Referring to FIGS. 9A through 9C, actuator 910 is, for example, a hydraulic actuator that controls the movement of loading arm 920 in multiple positions. Actuator 910 preferably is suited to lift 7,000 pounds in weight, for example. Longitudinally, loading arm 920 extends along the receiving side of infeed 320 and is sufficiently wide and long to support a log on rails 930. As shown, the outer side surface of loading arm 920 that faces staying mechanism 310 is curved, for example, like the outer surface of a section of a cylinder. Consequently, loading arm 920 can extend close to the edge of staying mechanism 310, as loading arm 920 moves in a curved path from the receiving position to the loading or ejecting position. In addition, as shown in FIG. 9B or 9C, loading arm 920 when in the loading or ejecting position is sufficiently tall to serve as a barrier that prevents logs on staying mechanism 310 from falling. Rails 930 of loading arm 920 substantially extend the full length of infeed 320 in accordance with an aspect of the invention. Similarly, rails 940 on frame 950 substantially extend the full length of the non-movable part of infeed 320.

Figure 9D:
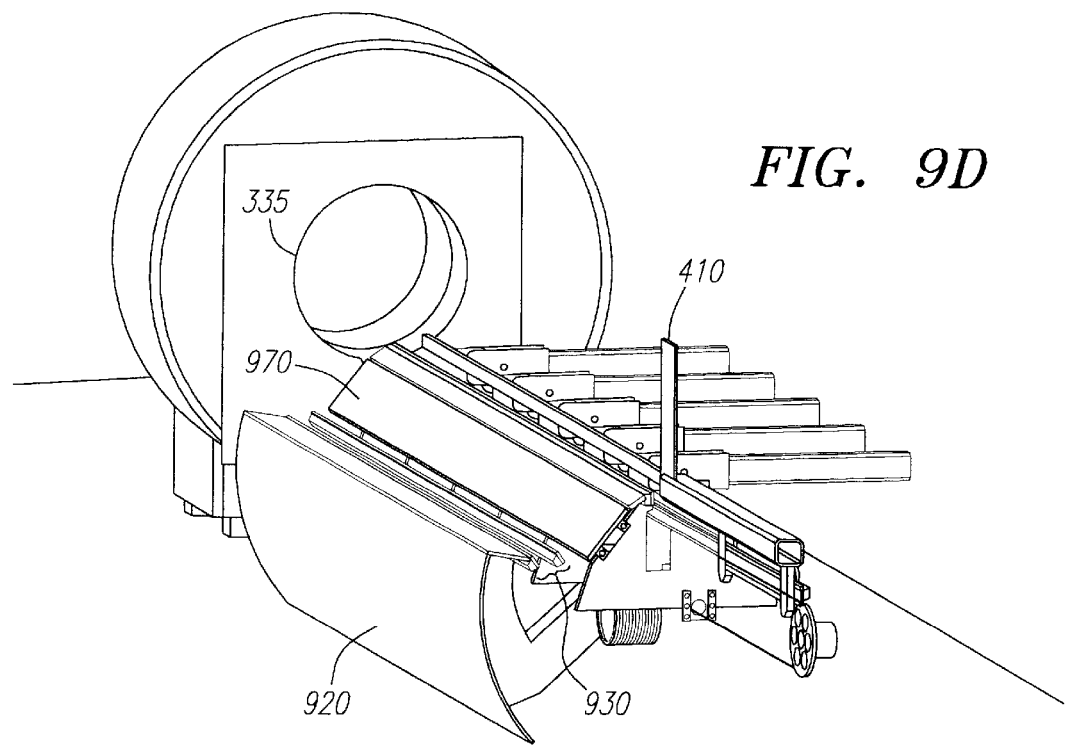
FIG. 9D is a perspective view of an embodiment of the system including a spring-loaded plate.

In certain embodiments, the non-movable part of infeed 320 also includes a spring-loaded plate 970 attached to frame 950 and extending along the side of loading arm 920. FIG. 9D is a perspective view of an embodiment of the system including a spring-loaded plate. As shown, the spring-loaded plate is positioned next to loading arm 920 to absorb the impact that loading of log 405 can cause to frame 950. Thus, when log 405 is loaded on the system as shown in FIG. 9A (e.g., when loading arm 920 is in a receiving position) log 405 rests on rails 930 and spring-loaded plate 970.

As shown in FIG. 9B, when loading arm 920 moves to the loading position, at step 830, rails 930 and 940 are aligned to form a portion of transport bed 420 that supports and guides log 405 through scanner 330. As log 405 is driven further through scanner 330, the weight of log 405 is gradually transferred from rails 930 and 940 to guide rails 510 and thereafter to rails of outfeed 340. A preferred embodiment of the system includes at least two pairs of coplanar rails for supporting the curved outer surface of log 405. In embodiments of the invention where scanner 330 includes guide rails 510, rails 930 and 940 are aligned to meet guide rails 510 such that a smooth continuous transport bed is provided for log 405 as it is being driven through scanner 330.

FIG. 9B illustrates loading arm 920, at step 830, in the loading position. Loading arm 920 raises log 405 onto a loading position so that log 405 rests on transport bed 420 made up of rails 930 and 940. As shown, log 405 is supported by transport bed 420 and is appropriately aligned so that log driver 410 can drive log 405 through scanner 330's aperture 335. In accordance with certain aspects of the invention, transport bed 420 is preferably coupled to an input sensor. The input sensor detects the presence of log 405 on transport bed 420. Referring to FIG. 5, the sensor is coupled through control system 626 to motion controller 622. Motion controller 622 controls the movement of log driver 410 along transport bed 420. When a log is initially loaded on the system, the log's exact position on transport bed 420 is determined through data derived from the input sensor, the transport bed 420, and motion controller 622.

In certain embodiments of the invention, a sensor included on transport bed 420 detects oversized logs (i.e., logs with a cylindrical volume or diameters larger than that of aperture 335). The sensor may be alternatively installed on other components of the system (e.g., log driver 410). Thus, step 840 determines whether the log loaded on transport bed 420 can go through aperture 335. If an oversized log is detected then, at step 870, the log is ejected from transport bed 420 as loading arm 920 is moved to an ejecting position, as shown in FIG. 9C. Moving loading arm 920 to ejecting position causes rails 930 and 940 to move out of alignment and shift transport bed 420 in an angle so that the oversized log is ejected from system 300. The input sensor in embodiments of the invention can be mounted on system 300's frame or any other suitable position. If the input sensor does not detect an oversized log then, at step 850, log driver 410 engages log 405 at one end. At step 860, log driver 410 drives log 405 through scanner 330 in a linear direction along transport bed 420.

Figure 10:
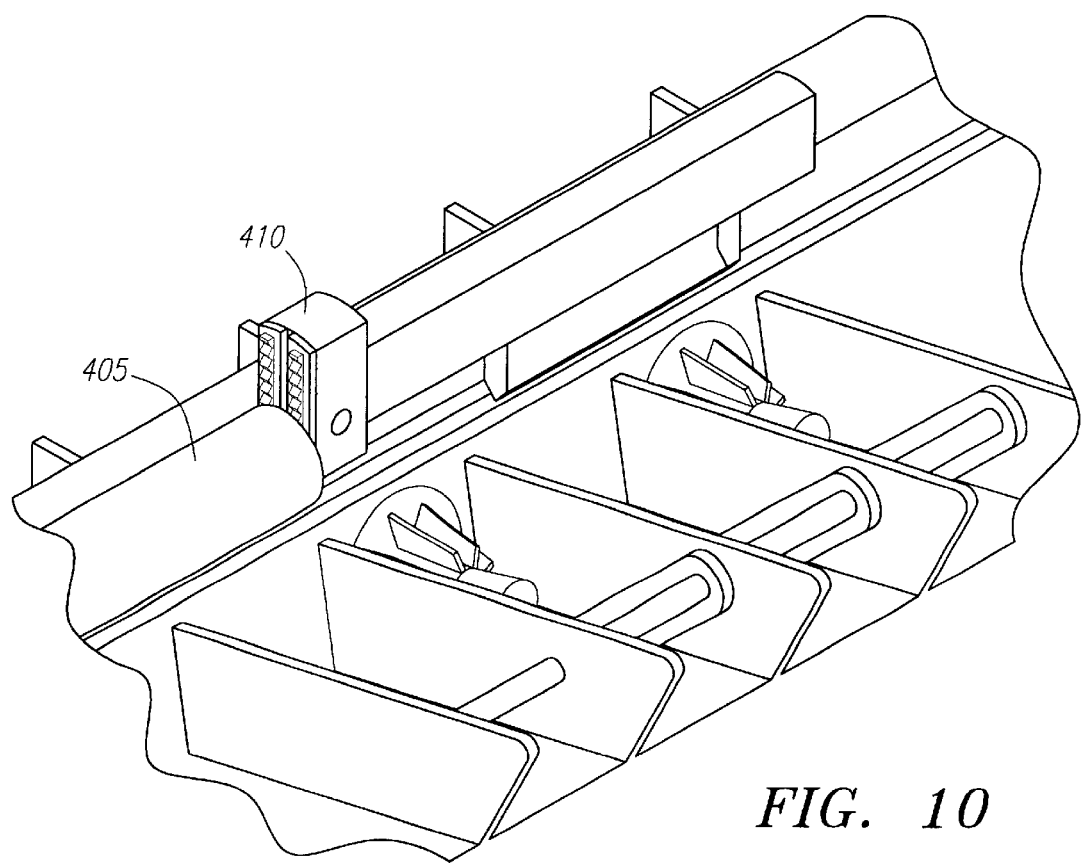
FIG. 10 is a perspective view of the log driver, according to one of the embodiments of the invention.

FIGS. 9D and 10 show perspective views of a log driver 410 suited for driving log 405, according to one or more embodiments of the invention. As shown in FIG. 10, the portion of log driver 410 that engages log 405 includes a toothed member to allow for a better grip on and stabilization of log 405. A motor drive engaged through a cable or chain driven mechanism posers log driver 410, for example, so that log driver 410 can retractably move forward and backward in a linear direction along transport bed 420. In embodiments of the system, log driver 420 is configured to generate sufficient force (e.g., 5,000 pounds) to move a log and to travel at the approximate speed of 20 centimeters per second. Log driver 420 is also configured to retract, in accordance with one aspect of the invention, at a proximate speed of 335 centimeters per second, for example. Other embodiments of the invention may include driving mechanisms with multiple log drivers installed in successive intervals such that a second log driver will be in position to engage a second log by the time the scanning process for the first log has been completed. This avoids the need for a retracting mechanism.

Figure 11:
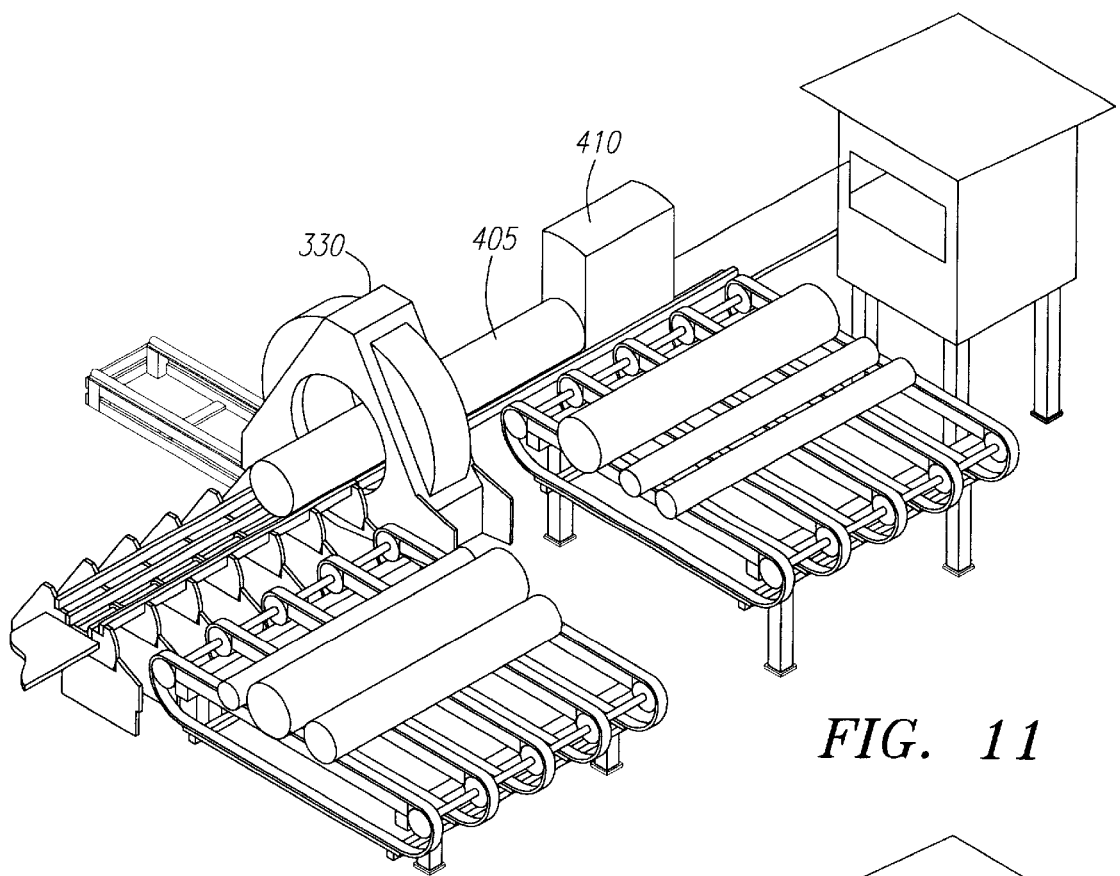
FIG. 11 is perspective view illustrating the log driver engaging a log and driving it through the scanner of the system, according to an embodiment of the invention.
Figure 12:
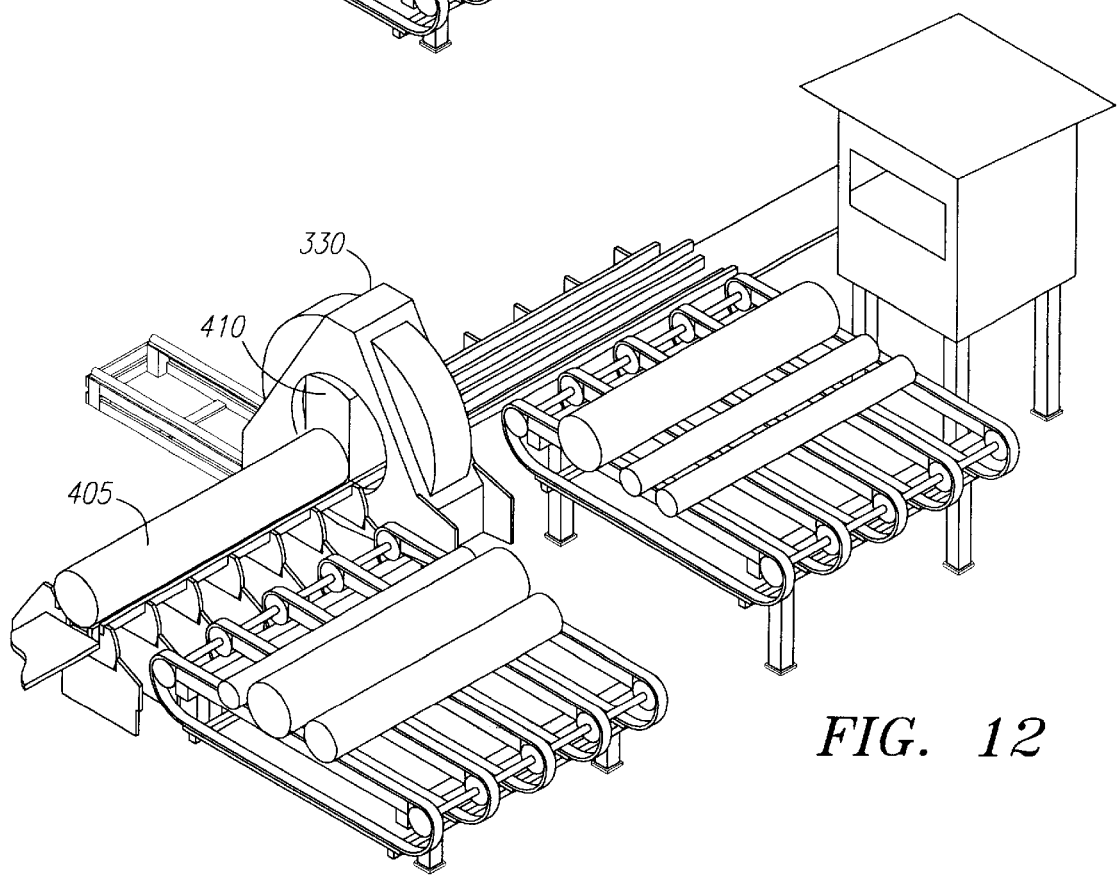
FIG. 12 is a perspective view illustrating the loading arm receiving a second log, as the log driver drives the first log through the scanner of the system, according to an embodiment of the invention.
Figure 13:
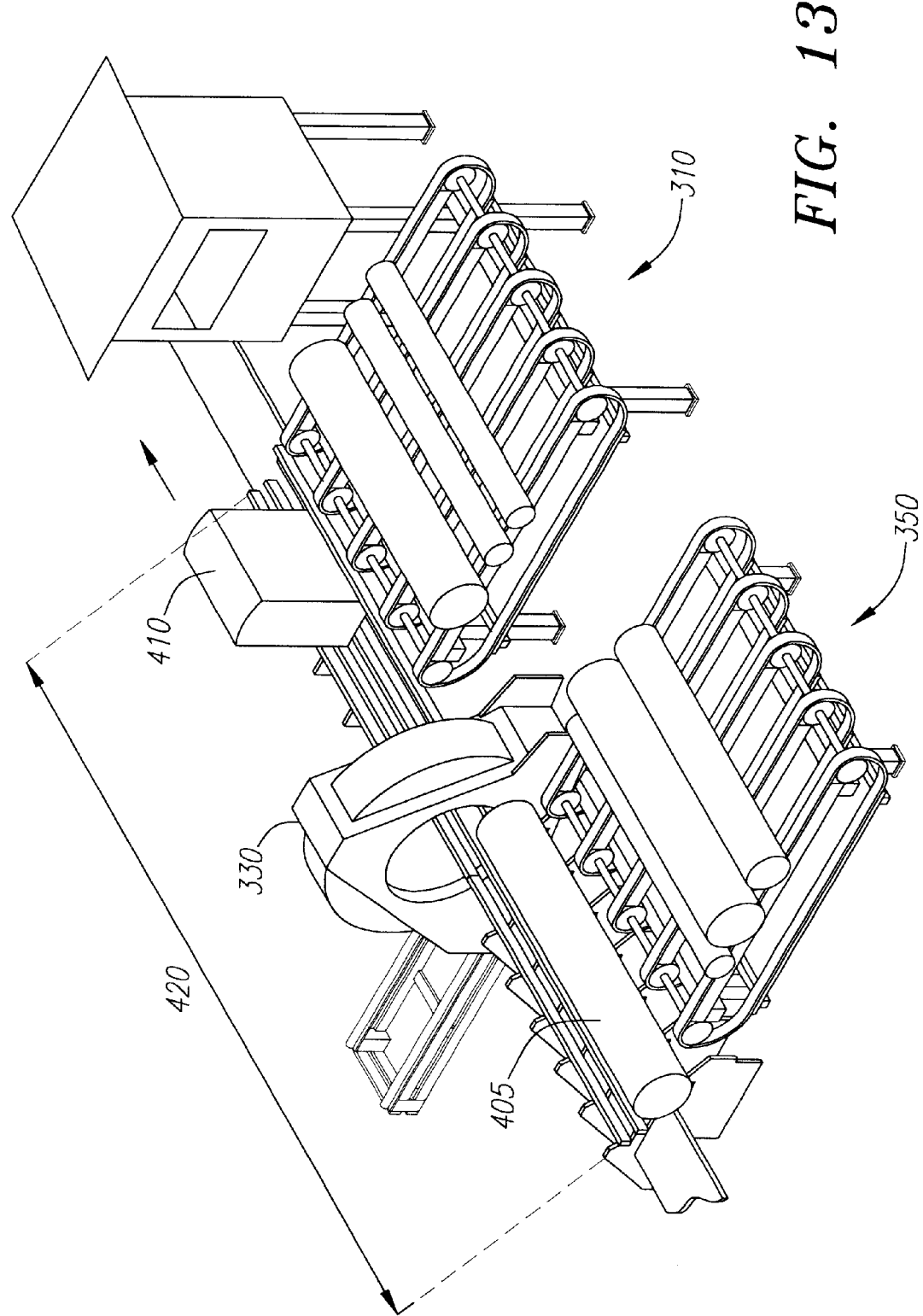
FIG. 13 is a perspective view illustrating the log driver as it retracts after scanning is completed.

FIG. 11 illustrates an embodiment of the system, where log driver 410 is driving log 405 through scanner 330 during the scanning process. A radiation tunnel covering the scan area is not shown in FIG. 11 for clarity, but can be included in certain embodiments. FIG. 12 illustrates system 300, after log 405 has been driven through and scanned by scanner 330. FIG. 13 illustrates log driver 410 retracting to its initial position as log 405 is being unloaded from outfeed 340. In certain embodiments of the system, outfeed 340 has the same configuration as that of infeed 320, but operates in reverse order. Thus, outfeed 340 is made up of movable and non-movable parts. The movable part, for example, includes an unloading arm operated by a hydraulic actuator that controls the movement of the arm in various positions.

The non-movable part and unloading arm of outfeed 340 each include rails that extend in a longitudinal direction. In combination, the rails on each part compose the portion of transport bed 420 that receives a log after the log is driven out of scanner 330. While a log moves on to outfeed 340, the unloading arm remains in a position with rails are parallel to and in a substantially horizontal planes with the corresponding rails of the non-movable part. In this position, the rails are aligned to form a stable transport bed 420 for receiving a log emerging from end of scanner 330. To unload the log, the unloading arm is lowered causing the transport bed tilt towards receiving mechanism 350. The created slope causes the log to roll down towards receiving mechanism 350.

In accordance with certain embodiments, a second log can be loaded on transport bed 420 via infeed 320 before or while the first log is unloaded from transport bed 420 via outfeed 340. The moving portions of infeed 320 and outfeed 340 are controlled and moved independently. Thus, for example, while the unloading arm of outfeed 340 moves to an unloading position, the loading arm of infeed 320 can move to a loading position. In an alternative embodiment, the movable portions of infeed 320 and outfeed 340 can be incorporated into an integrated hydraulic arm such that while the arm of outfeed 340 moves down to unload a log, the arm of infeed 320 moves down to receive another log. In addition to log driver 410, certain embodiments of the system also include an end unit (e.g., hold back dog). Structurally, the end unit is comparable with log driver 410. It engages a log at the end opposite to location of engagement of log driver 410 and provides sufficient resistance against the driving force of log driver 410 to further stabilize and secure a log's movement on transport bed 420.

In certain embodiments of the system, a marking device is included in the end unit and/or log driver 410 for placing one or more reference marks on the log. The reference marks indicate the orientation and positioning of a log on the system and can guide an automated sawing machine or a sawyer with cutting the log. In one embodiment, the marking device is a self-contained module that includes one or more spray heads for painting stripes on the ends of the log. The marking system can further include internal paint pots and one or more sensors for limiting over spray. In accordance with one or more embodiments, the marking system may include bar code applicators and readers. A bar code can be coded to include useful information about the log (e.g., length, size, weight, grade, etc.). Alternatively, memory storage mediums such as magnetic strips can be used to store more detailed information, such as optimal cutting solutions or image data for a scanned log.

Embodiments of this invention can be used in conjunction with an on-line sales model for presenting scanned logs for sale on a worldwide network, and a software system that efficiently presents internal features of a log in a two-dimensional data structure. One or more of these embodiments are described in U.S. patent application filed on Feb. 23, 2001, Ser. No. 09/792,650, the entire content of which is incorporated by reference, herein.

Thus, a system and method for analyzing and displaying the internal features of a log is described in conjunction with one or more embodiments. It should be understood, however, those system embodiments disclosed here are provided by way of example. Other methods or system architectures and implementations for transporting or scanning a log may be utilized. These and various adaptations and combinations of features of the embodiments disclosed are within the scope of the invention. The invention is defined by the following claims and their full scope of equivalents.

What is claimed is:

1. A system for non-intrusive analysis of internal features of an object, the system comprising:
    a transport bed comprising a plurality of parallel rails;
    scanning means for continuous scanning of an object as the object slides on the rails in an axial direction relative to the scanning means during the scanning of the object, the continuous scanning providing spiral scan data according to the internal features of the object, the object and the scanning means further moving in a rotational relationship with respect to one another; and
    construction means for processing the spiral scan data to generate one or more density distributions of one or more cross-sections of the object.

2. The system of claim 1, wherein the construction means generates images illustrating the internal features of the object.

3. The system of claim 1, wherein from the spiral scan data, the construction means constructs three-dimensional images of the object.

4. The system of claim 1, wherein the scanning means rotates around the object during scanning.

5. The system of claim 1, wherein the object revolves about its axis and the scanning means remains stationary during scanning.

6. The system of claim 1, wherein the scanning means comprises at least one x-ray source for projecting x-rays that traverse the object.

7. The system of claim 6, wherein the scanning means further comprises detector means for measuring the degree of attenuation of rays traversing the object.

8. The system of claim 1, further comprising a means for pushing the object in an axial direction in relation to the scanning means.

9. The system of claim 8, wherein the object is a log.

10. A method for non-intrusive analysis and display of inner features of an object comprising:
    continuously scanning an object while the object slides on parallel rails in an axial direction relative to a scanner, the scanner moving in a rotational relationship with respect to the object during the scanning;
    acquiring from the scanning, spiral scan data according to the internal features of the object; and
    processing the spiral scan data to construct one or more density distributions for one or more cross-sections of the object.

11. The method of claim 10, further comprising constructing one or more images based on the spiral scan data, the images illustrating the internal features of the object.

12. The method of claim 11, wherein the images provide one or more perspective views of the object.

13. The method of claim 12, where the one or more perspective views display the internal features of the object.

14. The method of claim 10, wherein the scanner rotates around the object.

15. The method of claim 10, wherein the object revolves about its axis in the scanner.

16. The method of claim 10, wherein the scanning comprises traversing the object with x-rays.

17. The method of claim 16, wherein the scanning further comprises identifying undesirable inner features of the object by measuring the degree of attenuation of the x-rays traversing the object.

18. The method of claim 10, wherein the rails each include a gap inside the scanner.

19. A system for non-intrusive analysis and display of inner features of an object, the system comprising:
    a scanning system comprising a gantry including scanning equipment configured to scan an object as the object continuously travels in an axial direction, through an aperture in the gantry;
    a transport bed extending through the aperture for supporting the object and directing the object's path of travel within the gantry; and
    a driver that is movable to contact a first end of the object and drive the object in the axial direction on the transport bed through the aperture of the gantry.

20. The system of claim 19, further comprising:
    a loading mechanism configured to load the object on the transport bed; and
    an unloading mechanism configured to unload the object from the transport bed.

21. The system of claim 19, further comprising a sensor that detects whether the object can fit through the aperture of the gantry.

22. The system of claim 21, further comprising an eject mechanism that unloads the object in response to the sensor detecting that the object is too large to fit through the aperture of the gantry.

23. The system of claim 22, further comprising a loading mechanism that includes rails that form a part of the transport bed when the loading mechanism is in a loading position.

24. The system of claim 23, wherein in the loading position, the rails included in the loading mechanism line up with rails included in the transport bed.

25. The system of claim 24, further comprising a marking mechanism that marks the object with a reference mark that indicates the orientation of the object with respect to the scanning system during scanning.

26. The system of claim 25, wherein the driver includes the marking mechanism.

27. The system of claim 26, further comprising an end unit in operational relationship with a second end of the object so as to firmly hold the object in a desired scanning position.

28. The system of claim 19, wherein the transport bed includes a gap in a part that extends through the aperture of the gantry, the gap being disposed opposite the scanning equipment so that scanning by the scanning equipment is unobstructed by the transport bed.

29. A method for non-intrusive analysis of an object, the method comprising:

scanning an object using a scanning system comprising a gantry, the gantry including an aperture and equipment configured to scan the object as the object moves through the scanning system; and continuously driving the object during the scanning process, through the aperture in a linear direction on a transport bed comprising parallel rails upon which the object slides during the scanning process.

30. The method of claim 29, further comprising loading the object onto the transport bed.

31. The method of claim 30, further comprising determining whether the object will fit through the aperture of the gantry.

32. The method of claim 31, further comprising unloading the object if it is determined that the object is too large to fit through the aperture of the gantry.

33. The method of claim 29, further comprising generating one or more images representing one or more cross-sections of the object, the images being generated from spiral scan data acquired during the scanning.

34. The method of claim 33, wherein the one or more images provide perspective views of the object.

35. The method of claim 33, further comprising reconstructing a density distribution for a cross-sectional of the object using a planar reconstruction technique on the spiral scan data.

36. The method of claim 35, further comprising constructing a perspective view of the object using an interpolation technique on the density distribution.

37. The method of claim 29, further comprising marking the object with a reference mark that indicates the orientation of the object during scanning.

38. A system for scanning a log, the system comprising:

a scanner, the scanner capable of providing spiral scan data of internal features of the log;

a transport bed including an infeed and an out feed, the infeed being configured to load a log on the transport bed, the out feed being configured to unload the log from the transport bed;

a log driver that pushes the log in an axial direction through the scanner on the transport bed from the infeed to the outfeed.

39. The system of claim 38, wherein the infeed comprises a movable part and a non-movable part, the movable part being configured to load the log onto the transport bed.

40. The system of claim 39, wherein the movable part and the non-movable part of the infeed include one or more rails, the rails in combination providing a part of the transport bed that receives the log.

41. The system of claim 40, wherein the movable part of the infeed comprises a loading arm that in a first position is lowered to receive a log for loading on the transport bed.

42. The system of claim 41, wherein raising the loading arm to a second position loads a log on the transport bed.

43. The system of claim 42, wherein raising the loading arm to a third position that is over the transport bed ejects a log from the transport bed.

44. The system of claim 43, wherein the loading arm is coupled to an actuator in relationship with a pivot point, such that when the actuator is activated the loading arm moves in a curved path around the pivot point to the first, second, and third positions.

45. The system of claim 41, wherein the non-movable part of the infeed comprises a spring loaded plate for absorbing shock to the system from loading a log, when the loading arm is in the first position.

46. The system of claim 38, wherein the outfeed comprises a movable part and a non-movable part, the movable part being configured to unload the log from the transport bed.

47. The system of claim 46, wherein the movable part and the non-movable part of the outfeed include one or more rails, the rails in combination providing a part of the transport bed that receives the log after it is scanned.

48. The system of claim 47, wherein the movable part of the outfeed includes an unloading arm configured to unload a log off the transport bed.

49. The system of claim 1, wherein in generating a density distribution of a said cross-section of the object, the construction means applies a planar reconstruction technique to the spiral scan data.

50. The method of claim 10, wherein the object is a log.

51. The system of claim 38, wherein the transport bed comprises a plurality of parallel rails, and the log slides on the rails during scanning by the scanner due to the pushing by the log driver.

52. The system of claim 51, wherein the scanner comprises a gantry that includes an aperture through which the rails extend.

53. The system of claim 38, wherein the scanner comprises a gantry that includes an aperture through which transport bed extends.

54. The system of claim 53, further comprising a sensor that detects whether the object can fit through the aperture of the gantry.

55. The system of claim 38, wherein the transport bed includes a gap over which the log moves, the gap being disposed so that scanning by the scanner is unobstructed by the transport bed.

56. The system of claim 35, wherein the scanner includes a portion that rotates around the log.

* * * * *